United States Patent [19]

Horn et al.

[11] Patent Number: 5,182,354

[45] Date of Patent: * Jan. 26, 1993

[54] TRANSPARENT, COMPACT POLYURETHANE CASTING COMPOSITIONS THAT ARE STERILIZABLE WITH SUPERHEATED STEAM, PROCESS FOR PREPARING SAME, AND THEIR USE, PARTICULARLY FOR MEDICAL-TECHNICAL ARTICLES

[75] Inventors: Peter Horn, Heidelberg; Walter Heckmann, Weinheim; Falko Ramsteiner, Ludwigshafen; Friedrich Gerold, Haar, all of Fed. Rep. of Germany

[73] Assignee: BASF Aktiengesellschaft, Ludwigshafen, Fed. Rep. of Germany

[*] Notice: The portion of the term of this patent subsequent to Sep. 3, 2008 has been disclaimed.

[21] Appl. No.: 507,694

[22] Filed: May 7, 1990

[30] Foreign Application Priority Data

Apr. 17, 1989 [DE] Fed. Rep. of Germany ....... 3912531

[51] Int. Cl.$^5$ ............................................. C08G 18/30
[52] U.S. Cl. ..................................... 528/60; 528/44; 528/48; 528/65; 528/66; 521/160; 560/351
[58] Field of Search ................... 528/44, 48, 60; 521/160; 560/351; 422/48

[56] References Cited

U.S. PATENT DOCUMENTS

| | | | |
|---|---|---|---|
| 4,118,411 | 10/1978 | Reiff et al. | 560/351 |
| 4,170,559 | 10/1979 | Kroplinski et al. | 422/48 |
| 4,224,164 | 9/1980 | Brauer et al. | 210/321.1 |
| 4,366,193 | 12/1982 | Linden et al. | 528/44 |
| 4,478,960 | 10/1984 | Buethe et al. | 521/160 |
| 4,814,103 | 3/1989 | Potter et al. | 528/48 |
| 5,045,623 | 9/1991 | Horn et al. | 528/60 |

Primary Examiner—John Kight, III
Assistant Examiner—Duc Druong
Attorney, Agent, or Firm—William G. Conger

[57] ABSTRACT

The invention relates to transparent, substantially compact polyurethane casting compositions, sterilizable with superheated steam, which are prepared by the reaction of:

A) modified diphenylmethane diisocyanates (A) that are liquid at 23° C. and are in turn are obtained by the reaction of
  1) a diphenylmethane diisocyanate isomer mixture, which in terms of 100 parts by weight comprises 60 to 90 parts by weight of 4,4'-diphenylmethane diisocyanate, 40 to 8 parts by weight of 2,4'-diphenylmethane diisocyanate, and 0 to 5 parts by weight of 2,2'-diphenylmethane diisocyanate with
  2) at least one polyoxypropylene polyol initiated with glycerine and/or trimethylol propane, having a molecular weight of 350 to 800 with a ratio of NCO:OH groups of 2.5:1 to 15:1, with
B) at least one compound having at least two reactive hydrogen atoms in the presence or absence of
C) catalysts, as well as to a process for preparing the polyurethane casting compounds and their use for medical-technical articles.

14 Claims, No Drawings

TRANSPARENT, COMPACT POLYURETHANE CASTING COMPOSITIONS THAT ARE STERILIZABLE WITH SUPERHEATED STEAM, PROCESS FOR PREPARING SAME, AND THEIR USE, PARTICULARLY FOR MEDICAL-TECHNICAL ARTICLES

The invention relates to transparent, substantially compact polyurethane (hereinafter also abbreviated as PU) casting compositions that are sterilizable with superheated steam, and which are prepared by the reaction of:
A) modified diphenylmethane diisocyanates (hereinafter abbreviated as MDI) which in turn are obtained by the reaction of:
 (1) an MDI mixture, which in terms of 100 parts by weight comprises 60 to 90 parts by weight of 4,4'-MDI, 40 to 8 parts by weight of 2,4'-MDI, and 0 to 5 parts by weight of 2,2'-MDI, with
 (2) at least one polyoxypropylene polyol initiated with glycerine and/or trimethylol propane, having a molecular weight of 350 to 800 with a ratio of NCO to OH groups of 2.5:1 to 15:1, with
B) at least one compound having at least two reactive hydrogen atoms, in the presence or absence of
C) catalysts.

PU casting systems are known and are summarily described for instance in the plastics handbook, "*Polyurethane*" [Polyurethanes], Vol. 7, 2nd Edition, 1983, pp. 392 ff, edited by Dr. G. Oertel, published by Carl Hanser Verlag, Munich and Vienna.

The use of PU casting compositions to produce molded articles for medical-technical equipment, in particular as an embedding material for embedding hollow fibers in dialyzers, is likewise not new, and is recommended as advantageous because of the easy handling of PU casting compositions and their low shrinkage during the curing process. For example, the following PU formulations are known, particularly for embedding hollow fibers:

U.S. Pat. No. 3,962,094 describes catalyst-free casting compositions, comprising ricinoleic-4,4'-MDI, ricinoleic tolylene diisocyanate or ricinoleic phenylene diisocyanate prepolymers with terminally positioned NCO groups and a cross-linking agent, which contains ricinus oil and/or an ester of an at least tetravalent alcohol and an aliphatic carboxylic acid having hydroxy or epoxy groups and at least 12 carbon atoms.

According to West German Patent Disclosure A 2 749 491 (equivalent to U.S. Pat. No. 4,170,559), the catalyst-free casting compositions comprise a prepolymer prepared from ricinus oil and polyoxypropylene glycol as well as 4,4'-MDI, and a cross-linking agent based on an ester of a multivalent alcohol having 2 or 3 hydroxyl groups and an aliphatic carboxylic acid with at least 12 carbon atoms and one or more hydroxyl and/or epoxy groups. The following suitable polyisocyanates for preparing the prepolymers are also named: 2,4- and 2,6-tolylene diisocyanate or phenylene diisocyanate. As cross-linking agents, monoesters and/or diesters of ethylene glycol and ricinoleic acid, trimethylol propane or trimethylol ethane are also possible.

Physiologically unobjectionable PU molding materials, particular for embedding hollow fibers in dialyzers, are prepared according to East German Patent 251 565 by the reaction of highly reactive, low-viscosity, storable mixed prepolymers, comprising solid, highly reactive aromatic diisocyanates and less-reactive liquid diisocyanates in a ratio by weight of 1:5 to 5:1 and polyols, with polyols selected from the group of ricinus oil and/or its transesterification products, high-purity polyesters and polyoxytetramethylene glycol. PU casting compositions comprising a PU prepolymer having terminally positioned isocyanate groups and a polyol mixture containing N,N,N',N'-tetrakis(2-hydroxypropyl)-ethylenediamine are the subject of U.S. Pat. No. 4,224,164. For preparing PU casting compositions for electrical equipment, mixtures of from 10 to 60% by weight of an ricinoleic acid ester and 90 to 40% by weight of a C2- to C6-hydrocarbon polymer with at least one hydroxyl group are used as the polyol component, according to U.S. Pat. No. 4,742,112. Two-component PU formulations that are not cytotoxic in the cured state and are suitable as casting compositions for separating apparatus, according to West German Patent Disclosure 3 048 529 (U.S. Pat. No. 4,332,927), comprise at least one NCO-terminated prepolymer, at least one polyol, and a catalytically active quantity of a dicarboxylated dialkyl tin compound. PU casting compositions catalyzed with tin-sulfur compounds for embedding cellulose hollow fibers in dialyzers are described in East German Patent 155 777.

The above-named PU casting compositions can be processed into medical-technical equipment and/or molded parts for such equipment and can be sterilized before use with ethylene oxide and/or with gamma rays. A disadvantage of this type of sterilization, however, is that residual traces of ethylene oxide can trigger allergies in some patients, and the gamma rays can form unidentifiable fission products, so that a certain risk to the patient's health from the dialysis cannot be entirely precluded. Yet the casting compositions known from the prior art are not sufficiently temperature- and chemical-resistant, and so cannot be subjected to superheated steam sterilization at a temperature of 121° C. over a time period of 20 minutes.

The object of the present invention is to develop transparent, substantially compact PU casting compositions that can be sterilized with superheated steam, for medical-technical articles, which are particularly suitable for embedding hollow fibers, especially those based on polysulfones, polycarbonates or cellulose, in dialysis cells, and which assure a firm bond with a housing, which as a rule comprises a bisphenol A polycarbonate. The PU casting composition must cure quickly, must not exhibit any interaction in the cured state with the embedded hollow fibers, and must not be toxic.

Unexpectedly, it proved possible to attain this object by the use of a modified diphenylmethane diisocyanate isomer mixture that is liquid at room temperature to prepare the PU casting compositions.

Hence, the subject of the invention is transparent, substantially compact PU casting compositions that are sterilizable with superheated steam, which are prepared by the reaction of
A) modified diphenylmethane diisocyanates, with
B) at least one compound having at least two reactive hydrogen atoms in the presence or absence of
C) catalysts,
and are characterized in that the modified diphenylmethane diisocyanates (A) are liquid at 23° C. and are prepared by the reaction of
 (1) a diphenylmethane diisocyanate isomer mixture, which in terms of 100 parts by weight comprises: 60 to 90 parts by weight, preferably 70 to 88 parts by weight, of 4,4'-diphenylmethane diisocyanate; 40 to 8 parts by weight, preferably 30 to 10 parts by weight, of 2,4'-diphenylmethane diisocyanate; and 0 to 5 parts by weight, preferably 0 to 3 parts by weight, of 2,2'-diphenylmethane diisocyanate with (2) at least one polyoxypropylene polyol having a molecular weight of 350 to 800, preferably from 400 to 700, obtained by using glycerine, trimethylol propane, or a mixture of glycerine and trimethylol propane as initiator molecules, in a ratio of NCO:OH groups of 2.5:1 to 15:1, preferably from 5:1 to 10:1.

The invention also relates to a process for preparing the transparent, substantially compact polyurethane casting compositions that are sterilizable by superheated steam, as well as to the use of the PU casting compositions for embedding hollow fibers preferably of polysulfones, polycarbonates or cellulose in dialyzers, for producing medical-technical articles, and also for bonding bioceramic coatings to endoprostheses.

Since the prior art mentions not only 1,5-naphthalene diisocyanate, tolylene diisocyanates and phenylene diisocyanates but also 4,4'-MDI, where the polyisocyanates are suitably made to react in the form of prepolymers, as suitable polyisocyanates for preparing the PU casting compositions, in particular for embedding hollow fibers in dialyzers, and since in this process polyurethanes that are sterilizable by superheated steam are not obtained, it was unexpected and unforeseeable that the selected, special MDI-isomer mixture, modified with the special polyoxypropylene triols in specific quantitative ratios, lend the cured PU casting compositions prepared from it an increased temperature resistance and improved hydrolysis resistance, so that the medical-technical articles can be sterilized in superheated steam without any problem.

It is also advantageous that the PU casting compositions according to the invention, in curing, do not attain the maximum temperature of 127° C., measured at the center point of a conically flaring 300 ml beaker of hard paper (made by Uniplast, located in 7417 Dillingen, Federal Republic of Germany) with a diameter of approximately 53 mm at the bottom and approximately 75 mm at the opening, into which 100 g of reaction mixture are poured, because the hollow fibers are damaged at temperature above 127° C.

(A) The modified MDIs (A) usable according to the invention suitably have a viscosity at 23° C. of 1000 to 3000 m.Pa.s, preferably 1200 to 2000 m.Pa.s, and an NCO content of 17 to 26% by weight, preferably 19 to 24% by weight, referred to the total weight, and are prepared by otherwise conventional processes by reacting the MDI isomer mixture with at least one polyoxypropylene triol at a temperature of suitably 60° to 100° C., preferably 70° to 90° C., and a reaction time of 0.5 to 3 hours preferably from 1 to 2 hours.

The following polyoxypropylene polyols are possible: polyoxypropylene polyols initiated with glycerine; polyoxypropylene polyols initiated with trimethylol propane; or mixtures of these polyoxypropylene polyols. Equally suitable are the polyoxypropylene polyols prepared by using a mixture of glycerine and trimethylol propane as initiator molecules, in which the ratios by weight of glycerine to trimethylol propane can be varied within wide limits. A glycerine-initiated polyoxypropylene triol having a molecular weight of approximately 420 is preferably used.

(B) As compounds (B) having at least two reactive hydrogen atoms, mixtures are preferably used that comprise: (B1) at least one polyhydroxyl compound having a molecular weight of from 1000 to 8500 and a functionality of 2 to 8; (B2) at least one low-molecular weight compound selected from the group consisting of ether-bridged diols and ester-bridged diols; and (B3) at least one cross-linking agent containing hydroxyl groups, the agent having a hydroxyl number of from 230 to 1900 and a functionality of from 3 to 8.

(B1) As polyhydroxyl compounds (B1) having a molecular weight of 1000 to 8500, preferably from 1500 to 5600 and in particular from 1800 to 4000 and a functionality of 2 to 8, preferably 2 to 4 and in particular 2 and/or 3, polyesterols and in particular polyetherols are preferably suitable. However, other polymers containing hydroxyl groups with ether or ester groups as bridge members are also possible, e.g., polyacetals, such as polyoxymethylenes and above all water-insoluble methylals, such as polybutanediol methylal and polyhexanediol methylal, and polycarbonates, particularly those prepared by transesterification from diphenyl carbonate and 1,6-hexanediol. The polyhydroxyl compounds named can be used as single components or in the form of mixtures.

Suitable polyesterols can be prepared for instance from dicarboxylic acids having from 2 to 12 and preferably 4 to 6 carbon atoms and multivalent alcohols. Examples of possible dicarboxylic acids are: aliphatic dicarboxylic acids, such as succinic acid, glutaric acid, adipinic acid, suberic acid, azelaic acid and sebacic acid, and aromatic dicarboxylic acids such as phthalic acid, isophthalic acid and terephthalic acid. The dicarboxylic acids can be used individually or as mixtures, for instance in the form of a mixture of succinic, glutaric and adipinic acid. For preparing the polyesterols, it may optionally be advantageous to use, instead of the dicarboxylic acids, the corresponding dicarboxylic acid derivatives, such as dicarboxylic acid monoesters or diesters having from 1 to 4 carbon atoms in the alcohol radical, dicarboxylic acid anhydrides or dicarboxylic acid dichlorides. Examples of multivalent alcohols are glycols having from 2 to 10 and preferably 2 to 6 carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol and dipropylene glycol. Depending on the properties desired, the multivalent alcohols can be used along with or optionally in mixtures with one another.

Also suitable are esters of the carbonic acid with the aforementioned diols, particularly those having from 4 to 6 carbon atoms, such as 1,4-butanediol and/or 1,6-hexanediol; condensation products of omega-hydroxycarboxylic acids, such as omega-hydroxycaproic acid; and preferably polymerization products of lactones, such as optionally substituted omega-caprolactones.

As polyesterols, the following are preferably used: ethanediol polyadipates, 1,4-butanediol polyadipates, ethanediol-1,4-butanediol polyadipates, 1,6-hexanediol neopentylglycol polyadipates, 1,6-hexanediol-1,4-butanediol polyadipates, and polycaprolactones.

The polyesterols have molecular weights of 1500 to 5600, preferably 1800 to 3500.

The polyetherols preferably used in particular may be prepared by known processes, such as anionic polymerization with alkali hydroxides, such as sodium hydroxide or potassium hydroxide, or alkali alcoholates, such as sodium methylate, sodium or potassium methylate or potassium isopropylate as catalysts, with the addition of at least one initiator molecule that contains from 2–8 and preferably 2–4 reactive hydrogen atoms in bonded form, or by cationic polymerization from one or more alkylene oxides having from 2 to 4 carbon atoms in the alkylene radical, with Lewis acids such as antimony pentachloride, boron fluoride etherate and others, or fuller's earth as catalysts.

Suitable alkylene oxides are for instance tetrahydrofuran, 1,3-propylene oxide, 1,2- or 2,3-butylene oxide, and preferably ethylene oxide and 1,2-propylene oxide. The alkylene oxides can be used individually, in alternation with one another or as mixtures. Possible initiator molecules include the following, for example: water; organic dicarboxylic acids, such as succinic acid, adipinic acid and/or glutaric acid; alkanolamines, such as ethanolamine, N-alkylalkanolamine, N-alkyldialkanolamines, such as N-methyl- and N-ethyl-diethanolamine; and preferably divalent or trivalent alcohols optionally containing ether bridges in bonded form, such as ethanediol, 1,2- and 1,3-propanediol, 1,4-butanediol, diethylene glycol, 1,5-pentanediol, 1,6-hexanediol, dipropylene glycol, 2-methyl-1,5-pentanediol and 2-ethyl-1,4-butanediol, glycerine, trimethylol propane, pentaerythritol, sorbitol and saccharose. The initiator molecules can be used individually or as mixtures.

Preferably, polyetherols of 1,2-propylene oxide and ethylene oxide are used, in which more than 50%, and preferably 60–80% of the OH groups are primary hydroxyl groups, and in which at least some of the ethylene oxide is disposed as a terminally positioned block. Such polyetherols can be obtained by polymerizing the 1,2-propylene oxide first to the initiator molecules, and then the ethylene oxide, or first copolymerizing all of the 1,2-propylene oxide in a mixture with part of the ethylene oxide and then subsequently polymerizing the rest of the ethylene oxide to it, or incrementally, first polymerizing part of the ethylene oxide, then all of the 1,2-propylene oxide, and finally the rest of the ethylene oxide to the initiator molecules.

Also, polyoxytetramethylene glycols, advantageously those having molecular weights of from 1000 to 3000, are particularly suitable.

The suitable polyetherols have molecular weights of from 1000 to 8500, preferably 1500 to 5600, and in particular 1800 to 4000. They can be used both individually and in the form of mixtures with one another.

Possible polyacetals containing hydroxyl groups are for instance those that can be prepared from glycols, such as diethylene glycol, triethylene glycol, 4,4'-dihydroxyethoxy-diphenyldimethylmethane, hexanediol and formaldehyde. Suitable polyacetals can also be prepared by polymerization of cyclic acetals.

Polycarbonates having hydroxyl groups that are possible include those of the type known per se that can be prepared for instance by the reaction of diols, such as 1,3-propanediol, 1,4-butanediol and/or 1,6-hexanediol, diethylene glycol, triethylene glycol or tetraethylene glycol with diarylcarbonates, such as diphenylcarbonates, or phosgene.

B2) As low-molecular divalent alcohols, the following glycols containing ester or ether groups as bridge members in bonded form are for instance possible: alkanediols having from 1–10 carbon atoms, preferably 2–6 carbon atoms, such as ethanediol, 1,2- or 1,3-propanediol, 2,2-dimethyl propanediol, 1,4-, 1,3-, or 2,3-butanediol, 1,5- or 2,5-pentanediol, 1,6-hexanediol, 2,2,5-trimethyl- or 2,2,5,5-tetramethyl-1,6-hexanediol; cycloalkanediols and alkylcycloalkanediols having from 6 to 19 carbon atoms, preferably 6 to 15 carbon atoms, such as 1,4-dihydroxycyclohexane, 1-hydroxymethyl-4-hydroxycyclohexane, 1,4-bis-(hydroxymethyl)-cyclohexane, 4,4'-dihydroxy-2,2-dicyclohexylmethane or -propane; glycols containing ester bridges in bonded form, such as 3-hydroxy-2,2-dimethylpropionic acid-2-hydroxyethylester, terephthalic acid-bisethylene glycol or 1,4-butanediol; and glycols containing ether bridges in bonded form having molecular weights up to 378, such as hydroxyalkylene ether of hydroquinone, such as 1,4-di-(B-hydroxyethyl-hydroquinone; oxyalkylene glycol having from 4–8 carbon atoms, such as diethylene, dipropylene or dibutylene glycol; as well as the corresponding higher-molecular oligomers thereof, such as dioxyethylene, trioxyethylene, dioxypropylene, trioxypropylene, dioxybutylene, trioxybutylene or tetraoxybutylene glycol. The dihydroxy compounds from the group of alkane-, cycloalkane-, alkylcycloalkyldiols and the corresponding glycols containing ester or ether bridges in bonded form can be used individually or as mixtures.

B3) As cross-linking agents containing hydroxyl groups having a hydroxyl number of 230 to 1900 and a functionality of 3 to 8, the following are preferably used: low-molecular tri- to octavalent, preferably tri- to tetravalent alcohols; trialkanolamines; polyoxyalkylene polyols having hydroxyl numbers of 350 to 950 initiated with alkylene diamines suitably having from 2 to 6 carbon atoms, or polyalkylene polyols having hydroxyl numbers of 230 to 1500 initiated with low-molecular tri- to octavalent alcohols. As trivalent to higher-valence alcohols, the following examples can be named: glycerine, trimethylol propane, pentaerythritol, 2,2,6,6-tetrahydroxymethyl-4-oxa-1,7-heptanediol (dipentaerythritol), dipentaerythritol, 3,3,7,7-tetrahydroxymethyl-5-oxanone (di-trimethylol propane) and sorbitol, trialkanolamines such as triethanolamine; and as polyoxyalkylene polyols initiated with alkylene diamines, the reaction products of 1,2propylene oxide, ethylene oxide or of mixtures of ethylene oxide and 1,2-propylene oxide, with aromatic or preferably aliphatic diamines, such as ethylene diamine, diethylene triamine, triethylene tetramine, 1,3-propylene diamine, 1,3- or 1,4-butylene diamine, 1,2-, 1,3-, 1–4, 1,5diamine, phenylene diamine, 2,4- and 2,6-tolylene diamine and 4,4'-, 2,4'- and 2,2'-diaminodiphenylmethane can be named. As polyether polyols, prepared from compounds of the group mentioned, the following are particularly important: N,N,N',N'-tetrakis(2-hydroxyethyl)ethylenediamine, N,N,N',N'-tetrakis(2-hydroxypropyl)-ethylenediamine, N,N,N',N'',N''-pentakis(2-hydroxypropyl)-diethylenetriamine, phenyldiisopropanolamine and higher alkylene oxide adducts of aniline. For preparing the polyoxyalkylene polyols with hydroxyl numbers of 230 to 1500, the aforementioned tri- to octavalent alcohols as initiator molecules and ethylene oxide and/or 1,2-propylene oxide are used.

The polyhydroxyl compounds B1-B3 are suitably used in such quantities that the mixture B comprises 1.0 mols of B1, 0.01 to 48 mols and preferably 2 to 20 mols of B2, and 0.01 to 32 mols and preferably 1.3 to 7 mols of B3.

It may optionally be advantageous, particularly when PU casting compositions with excellent surface quality are required, to use the following as a further constituent component (D), in addition to the aforementioned polyhydroxyl compounds B1-B3: glycerine monooleate, glycerine dioleate or an alkylepoxy stearate with a branchchained alkyl radical having at least 8 carbon atoms and preferably 10 to 20 carbon atoms, or mixtures of at least two of these compounds. If the glycerine mono- and/or dioleates and/or alkylepoxy stearates are used, these are suitably used in a quantity of 0.1 to 5% by weight, preferably 1 to 4% by weight, in terms of the total weight of A and B (i.e., the modified diphenylmethane diisocyanates plus the compounds having at least two reactive hydrogen additives thereon).

The preparation of the PU casting compositions can be performed in the presence or absence of catalysts. As suitable catalysts, dialkylcarboxylates such as dibutyl tin diacetate, dibutyl tin dilaurate and dicarboxylated dialkyl tin compounds of the kind described in West German Patent A 3 048 529 have proven themselves. If catalysts are used, they are typically used in a quantity of from 0.001 to 0.1 parts by weight, preferably 0.005 to 0.015 parts by weight, per 100 parts by weight of the constituent component (B).

To prepare the PU casting compounds, the modified MDIs (A) and compounds having at least two reactive hydrogen atoms (B) and optionally the constituent component (D) are made to react in the presence or absence of the catalysts (C), in such quantities that the equivalence ratio of NCO groups of the modified MDIs (A) to the sum of the reactive hydrogen atoms of component (B) and optionally (D) is 1:0.9 to 1.3, preferably 1:0.95 to 1.15, and in particular 1:0.98 to 1.05. To this end, the substantially completely degassed starting components are intensively mixed at temperatures of suitably 18° to 70° C., preferably 22° to 60° C., the reaction mixture is placed in a suitable molding tool, and is allowed to cure for a period of time of from 0.3 to 4 hours, preferably from 1 to 3 hours.

As already explained, the transparent, substantially compact PU casting compositions sterilizable with superheated steam are used in particular for embedding hollow fibers, preferably polysulfone, polycarbonate or cellulose hollow fibers in dialyzers; the dialysis equipment, and in particular the envelope for the dialysis filter suitably comprises a polycarbonate based on bisphenol A.

The PU casting compositions according to the invention are also suitable for producing medical-technical articles and for bonding bioceramic coatings to endoprostheses.

The PU casting compositions are nontoxic, transparent, exhibit no interaction with the hollow fibers, have pronounced adhesion to the polycarbonate, and can be cut well without destroying the embedded hollow fibers. Another essential factor for the use of the products is that the maximum temperature in curing under the conditions described is below 127° C., and the medical-technical articles can be subjected to superheated steam sterilization, without damage to the cured PU casting composition or to its adhesion to the polycarbonate housing.

Example 1

Preparation of the modified MDI:

In a four-liter three-necked flask, an MDI mixture comprising 1093.56 g of 4,4'-MDI and 156.23 g of 2,4'-MDI was heated to 80° C., and to it, while stirring, 250.21 g of a polyoxypropylene polyol initiated with glycerine and having a hydroxyl number of 400 was added, drop by drop, over a period of 60 minutes. To complete the reaction, it was stirred a further 60 minutes afterward at 80° C. The modified MDI obtained had an NCO content of 22.88% by weight and a viscosity at 25° C. of 1170 m.Pa.s.

Example 2

Preparation of the PU casting compositions

Component A: A mixture of 85.0 parts by weight of a polyoxypropylene (86% by weight) polyoxyethylene (14% by weight) triol having the hydroxyl number 28 and initiated with trimethylol propane, 2.0 parts by weight of a polyoxypropylene (85% by weight) polyoxyethylene (15% by weight) tetrol having the hydroxyl number 60 and initiated with ethylene diamine, 10.0 parts by weight of 1,4-butanediol, 3.0 parts by weight of glycerine and 0.01 parts by weight of dibutyl tin dilaurate.

Component B: Modified MDI was prepared as indicated in Example 1. 100 parts by weight of component A and 70.2 parts by weight of component B were intensively mixed at 23° C.; the reaction mixture was poured into a molding die and left to cure.

The gel time was 180 seconds and the maximum temperature 97.3° C., measured at the center of a conically flaring 800 ml hard paper beaker having a bottom diameter of 53 mm and a diameter at the opening of 75 mm, into which 100 ml of reaction mixture were poured. The PU casting composition was transparent and resistant to steam at 121° C. over a period of more than 20 minutes.

The superheated steam sterilization of dialyzers made of polycarbonate, equipped with polysulfone hollow fibers, prepared by centrifugal casting using the PU casting composition of example 2, caused no damage whatever.

Example 3

Preparation of the PU casting compositions

Component A: A mixture of 84.0 parts by weight of a polyoxypropylene (86% by weight) polyoxyethylene (14% by weight) triol having the hydroxyl number 28, and initiated with trimethylol propane, 14.0 parts by weight of 1,5-pentanediol, 2.0 parts by weight of glycerine and 0.015 parts by weight of dibutyl tin dilaurate.

Component B:: 75.2 parts by weight of modified MDI prepared in accordance with example 1.

To prepare the PU casting composition, the procedure was similar to that described in Example 2.

The gel time was 132 seconds and the maximum temperature 104° C.

The transparent product was undamaged by the superheated steam sterilization.

Example 4

Preparation of the PU casting compositions

Component A: A mixture of 80.0 parts by weight of a polyoxypropylene (86% by weight) polyoxyethylene (14% by weight) triol having the hydroxyl number 27, and initiated with trimethylol propane, 10.0 parts by weight of 1,4-butanediol, 10.0 parts by weight of a polyoxypropylene tetrol and initiated with ethylene diamine and having the hydroxyl number 768 and 0.005 parts by weight of dibutyl tin dilaurate.

Component B: 80.6 parts by weight of modified MDI prepared in accordance with example 1.

To prepare the PU casting composition, the procedure was similar to that described in Example 2.

The gel time was 171 seconds and the maximum temperature 94° C.

The transparent product was undamaged by the superheated steam sterilization.

Example 5

Preparation of the PU casting compositions

Component A: A mixture of 82.0 parts by weight of a polyoxypropylene (86% by weight) polyoxyethylene (14% by weight) triol having the hydroxyl number 26 and initiated with trimethylol propane, 10.0 parts by weight of 1,5-pentanediol, 1.0 parts by weight of glycerine, 7.0 parts by weight of a polyethylene triol initiated with trimethylol propane and having the hydroxyl number 944 and 0.015 parts by weight of dibutyl tin dilaurate.

Component B: 76.7 parts by weight of modified MDI prepared in accordance with example 1.

To prepare the PU casting composition, the procedure was similar to that described in Example 2.

The gel time was 130 seconds and the maximum temperature 102° C.

The transparent product was undamaged by the superheated steam sterilization.

Example 6

Preparation of the PU casting compositions

Component A: A mixture of 85.0 parts by weight of a polyoxypropylene (86% by weight) polyoxyethylene (14% by weight) triol having the hydroxyl number 26 and initiated with trimethylol propane, 5.0 parts by weight of 1,4-butanediol, 5.0 parts by weight of glycerine, 5.0 parts by weight of a polyoxypropylene tetrol initiated with ethylene diamine and having the hydroxyl number 768 and 0.01 parts by weight of dibutyl tin dilaurate.

Component B: 77.0 parts by weight of modified MDI prepared in accordance with example 1.

To prepare the PU casting composition, the procedure was similar to that described in Example 2.

The gel time was 161 seconds and the maximum temperature 97° C.

The transparent product was undamaged by the superheated steam sterilization.

Comparison Example: The procedure was similar to that given in example 1 of U.S. Pat. No. 4,224,164.

A clear, yellowish PU casting composition was obtained that separated from the polycarbonate housing under the conditions of superheated steam sterilization.

We claim:

1. A transparent, substantially compact polyurethane casting composition which is sterilizable with superheated steam, wherein the composition is produced by a method comprising the steps of:
   A. preparing a modified diphenylmethane diisocyanate wherein liquid at 23° C., the modified diphenylmethane diisocyanate being prepared by a process of reacting a diphenylmethane diisocyanate isomer mixture with at least one polyoxypropylene polyol wherein the diphenylmethane diisocyanate isomer mixture comprises from about 60 to about 90 weight percent of 4,4'diphenylmethane diisocyanate, from about 40 to about 8 weight percent of 2,4' diphenylmethane diisocyanate, and from 0 to 5 weight percent of 2,2'-diphenylmethane diisocyanate, and wherein the polyoxypropylene polyol has a molecular weight of from about 350 to about 800, the polyoxypropylene polyol having been produced by using at least one initiator selected from the group consisting of glycerine and trimethylol propane, and wherein the reaction of the diphenylmethane diisocyanate isomer mixture with the polyoxypropylene polyol is carried out with a ratio of NCO:OH of from about 2.5:1 to about 15:1, whereby the modified diphenylmethane diisocyanate is produced, and
   B. reacting the modified diphenylmethane diisocyanate with at least one compound having at least two reactive hydrogen atoms thereon.

2. A polyurethane composition as described in claim 1 wherein, in terms of 100 parts by weight, the diphenylmethane diisocyanate mixture comprises from about 60 to about 90 parts by weight of 4,4'-diphenylmethane diisocyanate, 40 to 8 parts by weight of 2,4'-diphenylmethane diisocyanate, and 0.1 to 5 parts by weight of 2,2'-diphenylmethane diisocyanate.

3. A polyurethane composition as described in claim 1 wherein the reaction of the modified diphenylmethane diisocyanate with the compound having at least two reactive hydrogen atoms is performed in the presence of a catalyst.

4. A transparent, substantially compact polyurethane casting composition which is sterilizable with superheated steam, as defined by claim 1, wherein the modified diphenylmethane diisocyanate is produced so that it has an NCO content of from 17 to 26% by weight, based on weight of the modified diphenylmethane diisocyanate.

5. A transparent, substantially compact polyurethane casting compositions, sterilizable with superheated steam, as defined by claim 1, wherein the modified diphenylmethane diisocyanate is produced so that it has a viscosity at 23° C. of from about 1000 to about 3000 m.Pa.s.

6. A transparent, substantially compact polyurethane casting composition, which is sterilizable with superheated steam, as described in claim 1, wherein the compounds having at least two reactive hydrogen atoms comprise:
   (a) at least one polyhydroxyl compound having a molecular weight of from 1000 to 8500 and a functionality of from 2 to 8,
   (b) at least one low molecular weight compound selected from the group consisting of ether-bridged diols and ester-bridged diols; and
   (c) at least one cross-linking agent containing hydroxyl groups, the agent having a hydroxyl number of from 230 to 1900 and a functionality of from 3 to 8.

7. A transparent, substantially compact polyurethane casting composition, which is sterilizable with superheated steam, as defined by claim 1, wherein the compounds having at least two reactive hydrogen atoms are a mixture comprising:
   (a) at least one polyetherol having a molecular weight of from 1000 to 8500 and a functionality of from 2 to 8,
   (b) at least one low-molecular dihydroxy compound, selected from the group consisting of alkanediols, cycloalkylenediols, and alkylcycloalkyldiols, and the corresponding glycols chich comprise at least one bridge member consisting of ester and ether groups in bonded form, and
   (c) at least one cross-linking agent selected from the group consisting of low molecular weight polyols having from 3 to 8 hydroxy groups thereon, trialkanolamines, polyoxyalkylene polyols initiated with alkylene diamines which have hydroxyl numbers of from 350 to 950, and polyoxyalkylene polyols having hydroxyl numbers from 230 to 1500 and initiated with low molecular weight polyols having from 3 to 8 hydroxy groups thereon 8. A transparent, substantially compact polyurethane casting composition which is sterilizable with superheated steam, as defined by claim 4, wherein the compounds having at least two reactive hydrogen atoms are a mixture comprising:
   (a) 1.0 mols of at least one polyhydroxyl compound having a molecular weight of from 1000 to 8500 and a functionality of from 2 to 8,
   (b) 0.01 to 48 mols of at least one low molecular weight compound selected from the group consisting of ether-bridged diols and ester-bridged diols, and
   (c) 0.01 to 32 mols of at least one cross-linking agent containing hydroxyl groups, the agent having a hydroxyl number of from 230 to 1900 and a functionality of from 3 to 8.

9. A method for making a transparent, substantially compact polyurethane casting composition which is sterilizable with superheated steam, as described in claim 1, wherein the method further comprises adding at least one additional member selected from the group consisting of glycerine monooleate, glycerin diooleate, and an alkylepoxy stearate having a branched alkyl radical having at least 8 carbon atoms thereon.

10. A method for making a transparent, substantially compact polyurethane casting composition which is sterilizable with superheated steam, as described in claim 9, wherein from 0.1 to 5 percent by weight of the additional member is used, based on the total weight of the modified diphenylmethane diisocyanates plus the compounds having at least two reactive hydrogen additives thereon.

11. A process as described in claim 1 wherein the reaction which produces the modified disphenylmethane diisocyanate is carried out so that the resulting modified diisocyanate has a viscosity at 23° C. of from 1000 to 3000 m.Pa.s and an NCO content of 17 to 26% by weight, based on the weight of the modified diisocyanate.

12. The method of using a transparent, substantially compact polyurethane coating composition to embed hollow fibers in dialysis equipment, wherein the polyurethane coating composition is a composition as described in claim 1.

13. The method of using a transparent, substantially compact polyurethane coating composition to produce at least one article selected from the group consisting of medical articles and technical articles, and wherein the polyurethane coating composition is a composition as described in claim 1.

14. The method of using a transparent, substantially compact polyurethane coating composition to bond bioceramic coatings to endoprostheses, wherein the polyurethane coating composition is a composition as described in claim 1.

* * * * *